US00PP12661P2

(12) United States Plant Patent
Oudolf

(10) Patent No.: US PP12,661 P2
(45) Date of Patent: May 28, 2002

(54) ACONITUM PLANT NAMED 'PINK SENSATION'

(75) Inventor: Piet Oudolf, De Hummelo (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/642,384

(22) Filed: Aug. 22, 2000

(51) Int. Cl.[7] ..... A01H 5/00
(52) U.S. Cl. ..... Plt./263
(58) Field of Search ..... Plt./263

(56) References Cited

PUBLICATIONS

GTITM UPOVROM Citation for 'Pink Sensation' as per QZ PBR 980543; Apr. 8, 1998.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Aconitum plant named 'Pink Sensation', characterized by its upright plant habit; dark green foliage; freely flowering habit; and pink flower color.

2 Drawing Sheets

BACKGROUND OF THE INVENTION

The present Invention relates to a new and distinct cultivar of Aconitum plant, botanically known as *Aconitum cammarum*, and hereinafter referred to by the cultivar name 'Pink Sensation'.

The new Aconitum is a product of a planned breeding program conducted by the Inventor in Hummelo, The Netherlands. The new Aconitum originated from a cross made by the Inventor between two unidentified selections of *Aconitum cammarum*, both not patented. The new Aconitum was selected by the Inventor in 1995 in a controlled environment from the resultant progeny on the basis of its pink flowers and short flowering stems.

Asexual reproduction of the new cultivar by divisions harvested in Hummelo, The Netherlands, has shown that the unique features of this new Aconitum are stable and reproduced true to type in successive generations.

SUMMARY OF THE INVENTION

Plants of the cultivar 'Pink Sensation' have not been observed under all possible environmental conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Pink Sensation'. These characteristics in combination distinguish 'Pink Sensation' as a new and distinct cultivar:

1. Upright plant habit.
2. Dark green foliage.
3. Freely flowering habit.
4. Pink flower color.

Compared to plants of the parent selections, plants of the new Aconitum are shorter and have a darker pink flower color.

Plants of the cultivar 'Pink Sensation' can be compared to plants of the *Aconitum cammarum* cultivar 'Roseum', not patented. Plants of the cultivar 'Pink Sensation' differ from plants of the cultivar 'Roseum' in the following characteristics:

1 1. Plants of the new Aconitum are stronger than plants of the cultivar 'Roseum'.

1 2. Plants of the new Aconitum are more freely flowering than plants of the cultivar 'Roseum'.

1 3. Flower color of plants of the new Aconitum is more pink than flower color of plants of the cultivar 'Roseum'.

BRIEF DESCRIPTION OF THE PHOTOGRAPHS

The accompanying colored photographs illustrate the overall appearance of the new Aconitum, showing the colors as true as it is reasonably possible to obtain in colored reproductions of this type. Colors in the photographs may differ slightly from the color values cited in the detailed botanical description which accurately describe the actual colors of the new Aconitum.

The photograph on the first sheet comprises a side perspective view of a typical flowering plant of 'Pink Sensation' grown in a container.

The photograph at the top of the second sheet is a close-up view of typical flowers of 'Pink Sensation'.

The photograph at the bottom of the second sheet is a close-up view of a typical leaf and a typical flower of 'Pink Sensation'.

DETAILED BOTANICAL DESCRIPTION

In the following description, color references are made to The Royal Horticultural Society Colour Chart except where general terms of ordinary dictionary significance are used. Plants used for the following description were about 12 months old and grown in 17-cm containers under field conditions which closely approximate commercial production conditions during the spring and summer in Hummelo, The Netherlands.

Botanical classification: *Aconitum cammarum* cultivar 'Pink Sensation'.

Parentage: Cross pollination of unidentified selections of *Aconitum cammarum*, not patented.

Propagation:

*Type cutting.*—By divisions.

*Rooting time.*—Divisions harvested in the spring develop roots in about 1 to 3 months.

*Root description.*—Tuberous.

Plant description:

*Form.*—Upright perennial flowering plant with deeply dissected leaves; geleate flowers arranged on erect racemes. Appropriate for 17-cm containers. One to three flowering racemes per plant.

*Crop time.*—After rooting, about 20 weeks are required to produce finished flowering plants in 17-cm containers.

*Plant height.*—About 70 cm.

*Plant diameter.*—About 27 cm.

*Vigor.*—Moderate to vigorous.

*Foliage description.*—Leaves simple, generally symmetrical, deeply dissected, and long-persisting. Length: About 9 cm. Width: About 12 cm. Shape: Deeply dissected, pedately lobed. Apex: Acute. Base: Acuminate. Margin: Incised to laciniate. Texture: Glabrous. Petiole: Length: About 4 cm. Diameter: About 2 mm. Color: Young foliage, upper surface: 137A to 137B. Young foliage, lower surface: 138B to 139C. Mature foliage, upper surface: 139A; veins, 139A to 139A. Mature foliage, lower surface: 138B; veins, 138B. Petiole color: 138B.

Flower description:

*Appearance.*—Numerous, single galeate, flowers arranged in racemes; zygomorphic. Flowers not persistent.

*Quantity of flowers.*—Freely flowering. During the flowering season, typically about 75 flowers per raceme.

*Natural flowering season.*—Early summer; in the Netherlands; flowering continuous.

*Fragrance.*—Not fragrant.

*Flower longevity on the plant.*—About 7 to 11 days.

*Flower size.*—Length: About 3.5 cm. Width: About 1.6 cm. Depth: About 2 cm.

*Flower buds (just before showing color).*—Length: About 1.4 cm. Diameter: About 9 mm. Shape: Oval to round. Color: 145A to 145B.

*Sepals.*—Appearance/arrangement: Five per flower, petaloid; one upper sepal, two lateral sepals and two lower sepals. Length: Upper sepal: About 2.5 cm. Lateral and lower sepals: About 2 cm. Width: Upper sepal: About 1.4 cm. Lateral sepals: About 2 cm. Lower sepals: About 1.5 cm. Shape: Upper sepal: Galeate; apex, acuminate; base, cuneate. Lateral sepals: Obovate to orbicular; apex, obtuse; base, cuneate. Lower sepals: Elliptic to obovate; apex, obtuse; base, cuneate. Margin: Entire. Texture: Smooth; short pubescence. Color: When opening, upper surface: 142B; margins, 186C to 186D. When opening, lower surface: 142B to 145A; margins, 186B. Fully opened, upper surface: 62D to 65C; margins, 65A; color does not fade with development. Fully opened, lower surface: 62C to 65B; margins, 65A.

*Petals.*—Quantity per inflorescence: Two. Length: About 4 mm. Width: About 9 mm. Shape: Linear. Apex: Acuminate. Base: Cuneate. Margin: Entire. Texture: Pubescent. Color: Upper surface: 137A. Lower surface: 137C.

*Pedicel.*—Length: About 1 cm. Angle: Erect to about 80° from vertical. Strength: Strong. Color: 137C.

*Peduncle.*—Length: About 70 cm. Diameter: About 3 mm. Aspect: Mostly upright. Texture: Very short hairs, more dense towards apex. Color: 137C to 138A.

*Reproductive organs.*—Stamens: Quantity: About 32. Anther length: About 6 mm. Anther color: Base, white; apex, 186C. Pollen amount: Scarce. Pollen color: Cream-colored. Pistils: Quantity: Two. Pistil length: About 2.3 mm. Style length: About 2 mm. Style color: 186C to 186D. Stigma color: 184A to 184B. Ovary color: 137C to 141A.

*Seed description.*—Length: About 1.2 mm. Diameter: About 0.9 mm. Color: Dark gray, darker than 201A.

Disease resistance: Plants of the new Aconitum have not been noted to be resistant to pathogens common to Aconitum.

It is claimed:

1. A new and distinct cultivar of Aconitum plant named 'Pink Sensation', as illustrated and described.

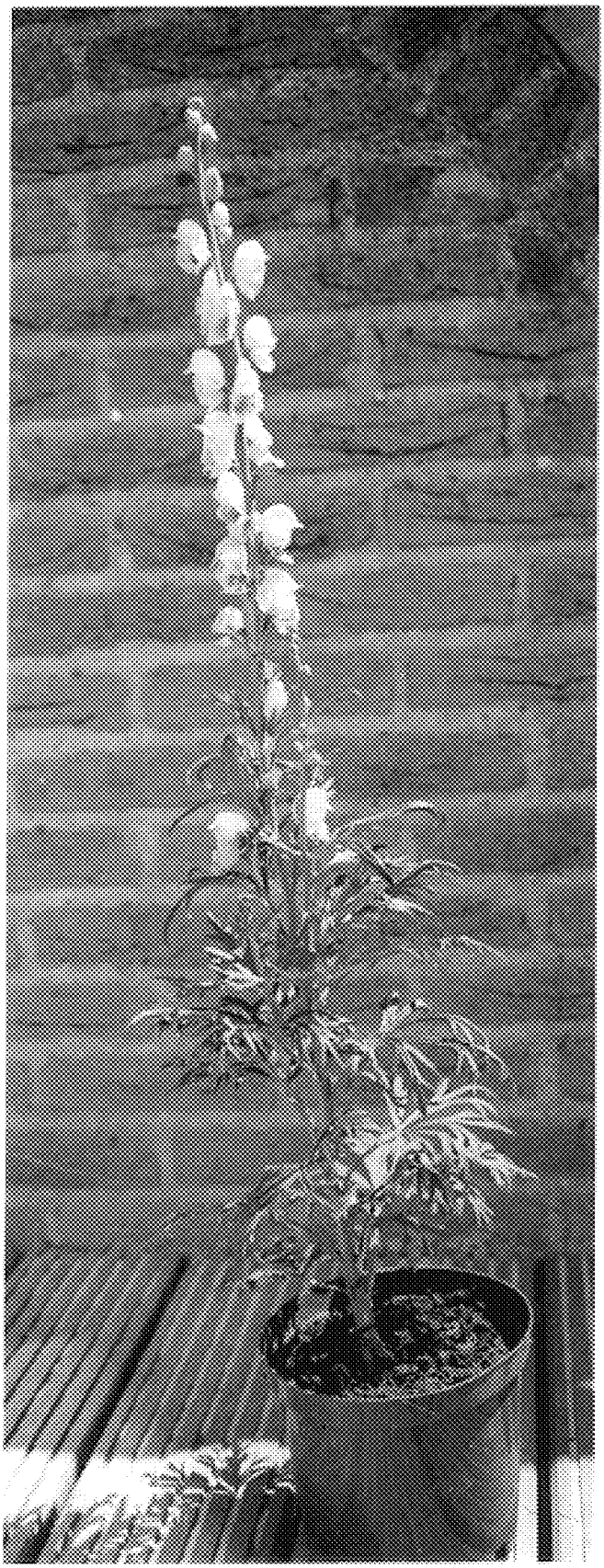

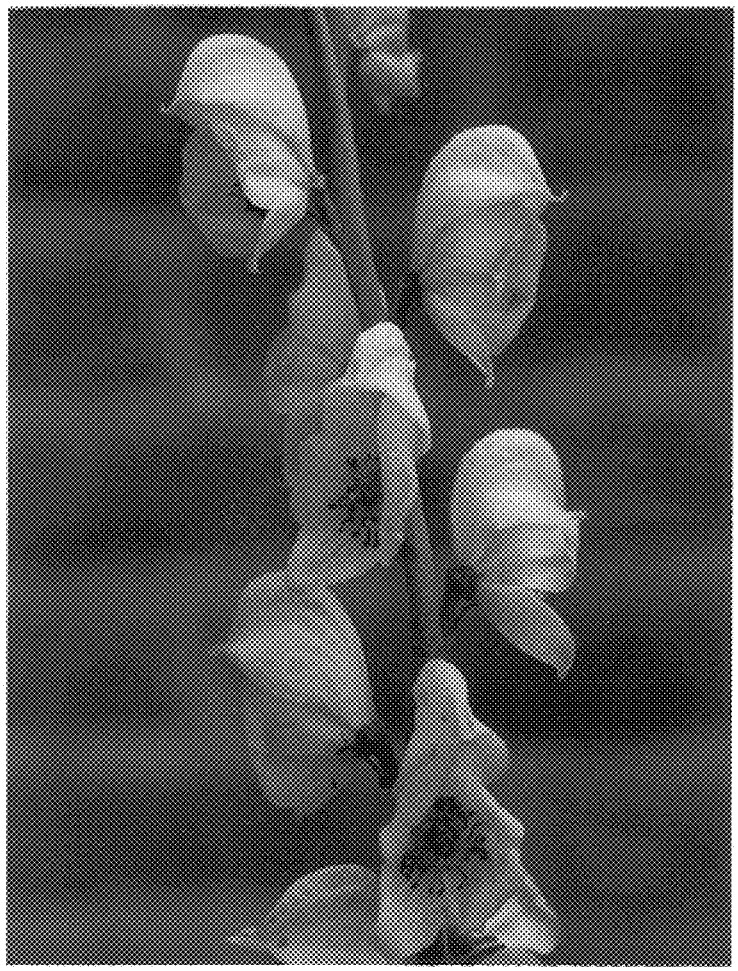
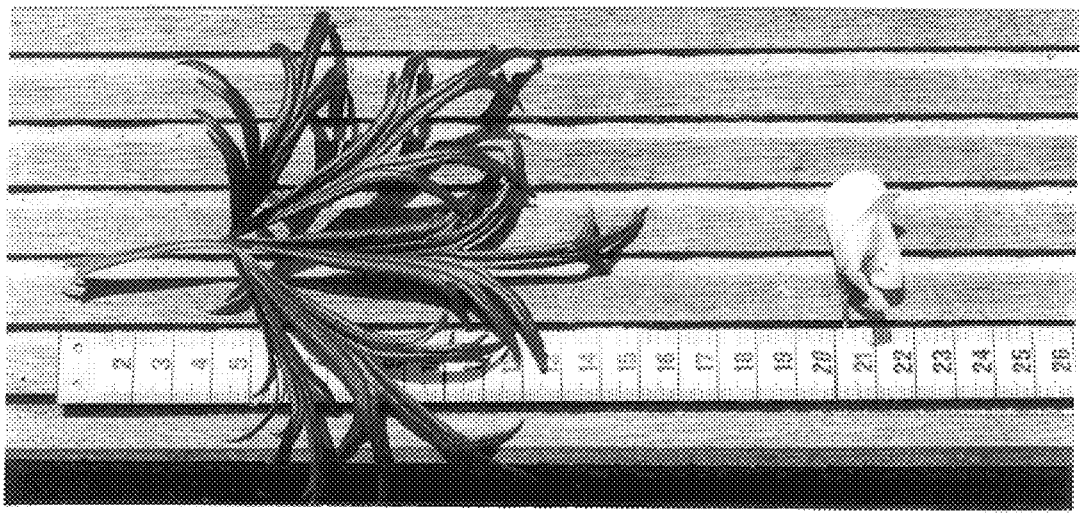

* * * * *